(12) United States Patent
Malinowski et al.

(10) Patent No.: US 8,788,043 B2
(45) Date of Patent: **\*Jul. 22, 2014**

(54) MINIMALLY INVASIVE METHODS FOR LOCATING AN OPTIMAL LOCATION FOR DEEP BRAIN STIMULATION

(71) Applicant: Boston Scientific Neuromodulation Corporation, Valencia, CA (US)

(72) Inventors: Zdzislaw B. Malinowski, Castaic, CA (US); Salomo Siilas Murtonen, San Gabriel, CA (US)

(73) Assignee: Boston Scientific Neuromodulation Corporation, Valencia, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 13/872,813

(22) Filed: Apr. 29, 2013

(65) Prior Publication Data

US 2013/0237994 A1  Sep. 12, 2013

Related U.S. Application Data

(63) Continuation of application No. 11/063,135, filed on Feb. 22, 2005, now Pat. No. 8,430,888.

(51) Int. Cl.
*A61N 1/05* (2006.01)
*A61N 1/36* (2006.01)

(52) U.S. Cl.
CPC .............. *A61N 1/05* (2013.01); *A61N 1/0534* (2013.01); *A61N 1/36071* (2013.01); *A61N 1/36082* (2013.01)
USPC .......................................... 607/45; 607/116

(58) Field of Classification Search
CPC ... A61N 1/05; A61N 1/0534; A61N 1/36071; A61N 1/36082
USPC ...................................... 606/129; 607/45, 116
See application file for complete search history.

(56) References Cited

U.S. PATENT DOCUMENTS

| 5,788,713 | A | 8/1998 | Dubach et al. |
|---|---|---|---|
| 6,006,134 | A | 12/1999 | Hill et al. |
| 6,011,996 | A | 1/2000 | Gielen et al. |
| 6,253,109 | B1 | 6/2001 | Gielen |
| 6,301,492 | B1 | 10/2001 | Zonenshayn |
| 6,343,226 | B1 | 1/2002 | Sunde et al. |
| 6,353,672 | B1 | 3/2002 | Rhoads |
| 6,353,762 | B1 | 3/2002 | Baudino et al. |
| 6,461,372 | B1 | 10/2002 | Jensen et al. |
| 2004/0006350 | A1 | 1/2004 | Hogg et al. |

(Continued)

OTHER PUBLICATIONS

Office Action dated Jan. 29, 2007, for related U.S. Appl. No. 11/063,110, filed Feb. 22, 2005, Inventor Zdzislaw B. Malinowski (6pages).

(Continued)

*Primary Examiner* — Tammie K Heller
(74) *Attorney, Agent, or Firm* — Vista IP Law Group LLP

(57) ABSTRACT

Methods of locating an optimal site within a brain of a patient for deep brain stimulation include positioning a guiding cannula in a lumen of a main cannula, passing a microelectrode through a lumen of the guiding cannula into the brain, adjusting an insertion depth and a longitudinal angle of the guiding cannula such that the microelectrode locates the optimal site for the deep brain stimulation, and passing a distal end of a macroelectrode or a deep brain stimulation lead through the lumen of the main cannula and into the brain at the optimal site.

23 Claims, 16 Drawing Sheets

(56) References Cited

U.S. PATENT DOCUMENTS

2004/0039338 A1 2/2004 Lee et al.
2006/0190054 A1 8/2006 Malinowski et al.
2006/0190055 A1 8/2006 Malinowski et al.

OTHER PUBLICATIONS

Amendment/Response dated Apr. 30, 2007, for related U.S. Appl. No. 11/063,110, filed Feb. 22, 2005, Inventor Zdzislaw B. Malinowski (11pages).

Office Action dated May 24, 2007, for related U.S. Appl. No. 11/063,110, filed Feb. 22, 2005, Inventor Zdzislaw B. Malinowski (14pages).

Amendment and Response dated Sep. 24, 2007, for related U.S. Appl. No. 11/063,110, filed Feb. 22, 2005, Inventor Zdzislaw B. Malinowski (9 pages).

"David Kopf Instruments—Electrode Manipulators", http://www.kopfinstruments.com/Stereotaxic/Emanipulators.htm. May 22, 2007 (5pages).

"Kopf—Model 1404 Heavy-Duty Research Model Stereotaxix for Cats and Monkeys", http://www.kopfinstruments.com/Stereotaxic/1404.html. May 22, 2007 (2pages).

FIG. 4A          FIG. 4B

MINIMALLY INVASIVE METHODS FOR LOCATING AN OPTIMAL LOCATION FOR DEEP BRAIN STIMULATION

RELATED APPLICATIONS

The present application is a continuation of U.S. patent application Ser. No. 11/063,135, filed Feb. 22, 2005 (now U.S. Pat. No. 8,430,888), which application is herein incorporated by reference in its entirety.

BACKGROUND

Deep brain stimulation (DBS) and other related procedures involving the implantation of leads and catheters in the brain are increasingly used to treat such conditions as Parkinson's disease, dystonia, essential tremor, seizure disorders, obesity, depression, motor control disorders, and other debilitating diseases. During these procedures, a catheter, lead, or other medical device is strategically placed at a target site in the brain. Locating the "best" or optimal site in the brain for deep brain stimulation can be a painstaking procedure.

Implantation of a lead for DBS generally involves the following preliminary steps: (a) anatomical mapping and (b) physiological mapping. Anatomical mapping involves mapping segments of an individual's brain anatomy using non-invasive imaging techniques, such as magnetic resonance imaging (MRI) and computed axial tomography (CAT) scans. Physiological mapping involves locating the brain site to be stimulated. Step (b) can be further divided into: (i) preliminarily identifying a promising brain site by recording individual cell activity with a microelectrode and (ii) confirming physiological stimulation efficacy of that site by performing a test stimulation with a macroelectrode or microelectrode.

Microelectrode recording is generally performed with a microelectrode recording (MER) system. The MER system includes a small diameter electrode with a relatively small surface area optimal for recording single cell activity. The microelectrode may essentially be an insulated wire that has at least the distal portion uninsulated to receive electrical signals. The microelectrode functions as a probe to locate an optimal site in the brain for deep brain stimulation. Activity detected through the microelectrode is recorded by the MER system. Since a number of attempts may be required to locate the optimal site, it is desirable that the microelectrode be as small as possible to minimize trauma when the microelectrode is introduced into the brain, in some cases, multiple times.

Once an optimal site in the brain for deep brain stimulation has been identified by the microelectrode recording, a macroelectrode is used to test whether the applied stimulation has the intended therapeutic effect. Once macrostimulation confirms that stimulation at the optimal site provides the intended therapeutic effect, the macroelectrode is withdrawn from the brain and a DBS lead is permanently implanted at the optimal site in the brain for deep brain stimulation.

There are a number of commercially available MER systems used in deep brain stimulation. One exemplary MER system permits the neurosurgeon to simultaneously record an output from five different microelectrodes, referred to as "five-at-a-time." In this approach, five microelectrodes are advanced into the brain at the same time and at the same speed. This presents obvious advantages. The set-up time may be proportionately cut, since the chance of locating an optimal stimulation site theoretically increases by five fold. However, the size and configuration of this system is more likely to cause damage to brain tissue. For instance, because the microelectrodes in a "five-at-a-time" system are placed relatively close to each other, two of these electrodes may sometimes "capture" a blood vessel between them. This may result in vessel punctures and may lead to intracranial bleeding. In contrast, when a single microelectrode is used, a blood vessel can often escape injury because the vessel can deflect away from the microelectrode, or vice-versa. Thus, some neurosurgeons choose to use an MER system with only a single microdrive, advancing one microelectrode at a time until an optimal stimulation site is found.

The recorded output of a microelectrode advanced along a path through the brain is referred to as a recording tract. Some neurosurgeons average four to five microelectrode recording tracts before they decide on an optimal site in the brain for deep brain stimulation. Other neurosurgeons only use one recording tract, which cuts surgery duration, but which may not locate the optimal stimulation site. Without optimal electrode placement, the DBS lead may need to be driven at a higher current to produce the desired therapeutic effect. This, however, can cause the device battery to be drained more quickly. In addition, the use of higher currents can increase the risk of undesirable side effects such as dysarthria (slurred speech) and abulia (an abnormal inability to make decisions or to act).

Each of these MER systems applies the conventional surgical procedure of creating multiple microelectrode tracts until an optimal site for deep brain stimulation is found within the brain. On average, a single microelectrode recording tract takes approximately thirty minutes to perform. Each microelectrode recording tract requires placement of the microelectrode via a larger diameter insertion cannula through viable brain tissue. Each time an object is inserted into the brain there is approximately a five percent risk of hemorrhage. Creating multiple tracts increases the risk for intracranial bleeding, duration of operation, post-operative infection, and operative risk. Creating new tracts is fraught with misalignment/misplacement problems because the introduction cannulas may not always trace the exact pathways desired.

SUMMARY

Methods of locating an optimal site within a brain of a patient for deep brain stimulation include positioning a guiding cannula in a lumen of a main cannula, passing a microelectrode through a lumen of the guiding cannula into the brain, adjusting an insertion depth and a longitudinal angle of the guiding cannula such that the microelectrode locates the optimal site for the deep brain stimulation, and passing a distal end of a macroelectrode or a deep brain stimulation lead through the lumen of the main cannula and into the brain at the optimal site.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 4A is a side view of an exemplary depth adjustment mechanism according to principles described herein.

FIG. 4B is a half cross-sectional view of the depth adjustment mechanism taken along the perspective line indicated in FIG. 4A according to principles described herein.

Throughout the drawings, identical reference numbers designate similar, but not necessarily identical, elements.

DETAILED DESCRIPTION

The present application is related to an application entitled "Minimally Invasive Systems for Locating an Optimal Location for Deep Brain Stimulation" to Malinowski et al., client docket number AB-333U1, which application is to be filed on the same day as the present application. The AB-333U1 application is incorporated herein by reference in its entirety.

Minimally invasive methods and systems for making a precise identification of an optimal site within the brain of a patient for deep brain stimulation (DBS) are described herein. A main cannula is first coupled to a stereotactic instrument, which is configured to mount on the head of a patient. The main cannula has a distal end that is inserted into the brain. A guiding cannula is then passed through a lumen of the main cannula and inserted further into the brain starting at an initial insertion depth determined by the insertion depth of the main cannula. A microelectrode may then be passed through the guiding cannula and positioned within the brain. The insertion depth and/or longitudinal angle of the guiding cannula may be adjusted with a depth adjustment mechanism and/or a longitudinal angle adjustment device, respectively, such that the microelectrode locates the optimal site for the deep brain stimulation. Once the microelectrode locates the optimal site for deep brain stimulation, the exact coordinates of the optimal site for deep brain stimulation are calculated. These coordinates may then be used to subsequently insert a macroelectrode or deep brain stimulation lead within the brain and provide macrostimulation and/or deep brain stimulation at the optimal site for deep brain stimulation.

In the following description, for purposes of explanation, numerous specific details are set forth in order to provide a thorough understanding of the present systems and methods.

It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

The term "deep brain stimulation" or "DBS" will be used herein and in the appended claims, unless otherwise specifically denoted, to refer to any therapeutic stimulation that may be applied to any stimulation site within the brain of a patient. The deep brain stimulation may include electrical stimulation and/or drug stimulation.

Figure 1:
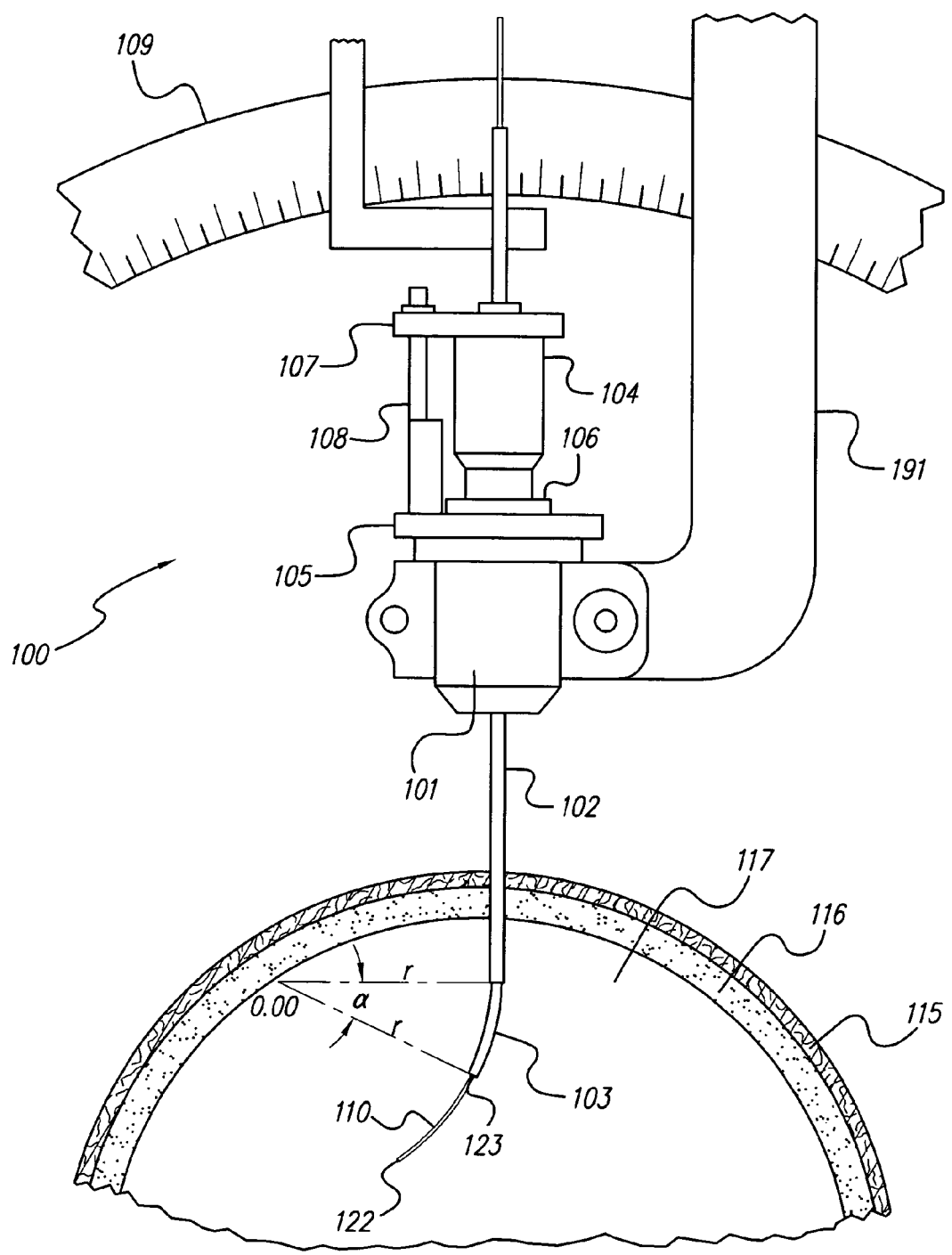
FIG. 1 shows a schematic diagram of an exemplary deep brain stimulation (DBS) lead insertion system according to principles described herein.

FIG. 1 shows a schematic diagram of an exemplary deep brain stimulation (DBS) lead insertion system (100). The DBS lead insertion system (100) may include a number of components. The example shown in FIG. 1 is merely illustrative and components may be removed, added to, or replaced as best serves a particular DBS application. The components of the DBS lead insertion system (100) may be made out of any suitable material(s) as best serves a particular DBS application. For example, some or all of the components of the DBS lead insertion system (100) may be made out of stainless steel or other biocompatible materials such as titanium alloy.

The exemplary DBS lead insertion system (100) of FIG. 1 includes a main base (101) configured to support a number of additional components of the DBS lead insertion system (100) as will be described below. The main base (101) is coupled to a stereotactic frame (109) using a mounting structure (191). The stereotactic frame (109) holds the components of the DBS lead insertion system (100) during a DBS procedure. FIG. 1 also shows a skull (115), dura mater (116), and brain (117) of a patient.

As shown in FIG. 1, a main cannula (102) is inserted into the brain (117) and is configured to allow passage of a guiding cannula (103), sometimes called a microstimulator-guiding cannula, into the brain (117). The guiding cannula (103), in turn, is configured to allow passage of a microelectrode (110) into the brain (117). The microelectrode (110) may be used to perform microelectrode recording or probing of individual cell activity to locate an optimal site within the brain (117) for deep brain stimulation. A macroelectrode and/or a DBS lead may subsequently be inserted into the brain (117) at the optimal site via the main cannula (102) to provide test stimulation (macrostimulation) and/or deep brain stimulation, as will be explained in more detail below. The DBS lead may be a lead having a number of electrodes for electrical stimulation of the brain. The DBS lead may alternatively be a catheter for providing drug stimulation to the brain. Hence, as used herein and in the appended claims, unless otherwise specifically denoted, the term "DBS lead" will be used to refer to any lead having a number of electrodes or to a catheter.

The DBS lead insertion system (100) may further include a depth adjustment mechanism (104) for adjusting the depth of the guiding cannula (103) within the brain (117) and a longitude adjustment plate (105) for adjusting the longitudinal position of the guiding cannula (103) within the brain (117). A longitudinal locking mechanism (106), which may be a longitudinal locking nut, locks the microelectrode (110) in a particular longitudinal position. A guiding plate (107) and a retaining rail (108) may also be provided to maintain a precise longitudinal direction of the guiding cannula (103). Each of the components of the DBS lead insertion system (100) shown in FIG. 1 will be explained in more detail below.

Figure 2:
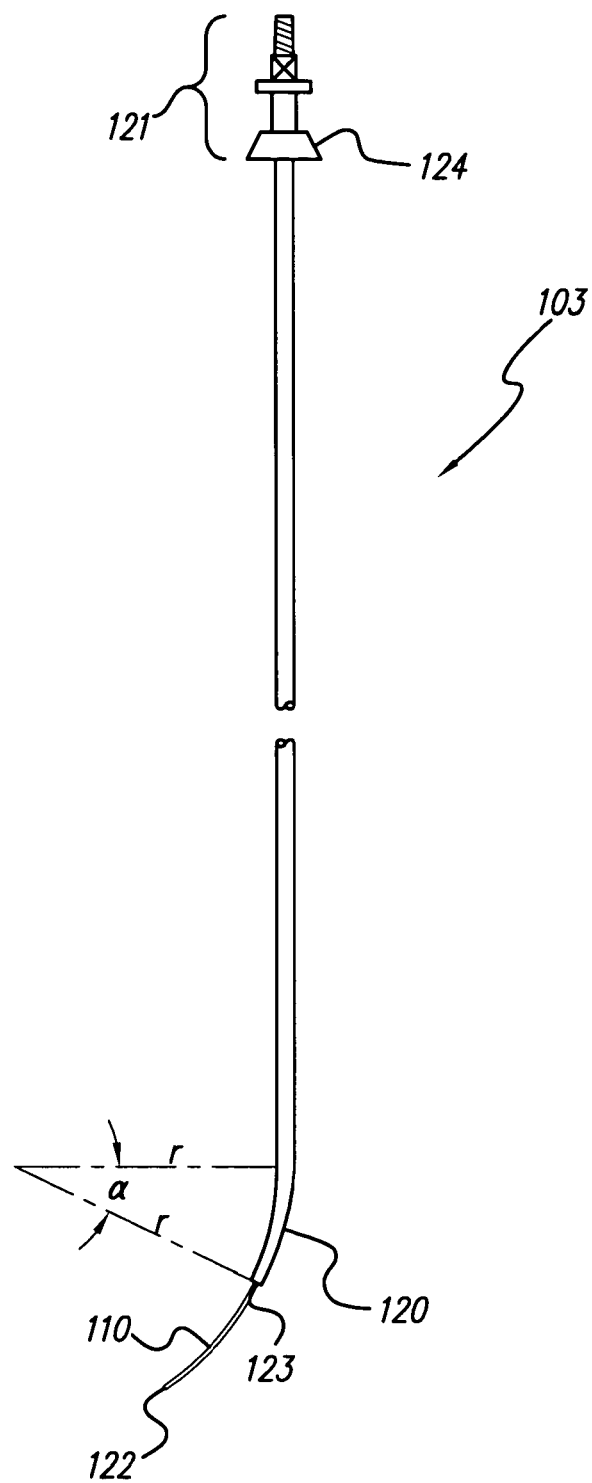
FIG. 2 illustrates an exemplary guiding cannula according to principles described herein.

FIG. 2 illustrates an exemplary guiding cannula (103). The guiding cannula (103) may be prefabricated and made from a Nitinol alloy or any other suitable material configured to retain its shape even after temporary or accidental deformation. Nitinol alloys are known for their superelasticity and shape memory properties. Nitinol alloys may therefore be configured to have an optimum superelastic behavior at body temperature.

As shown in FIG. 2, the guiding cannula (103) has a cylindrical tubular form. A proximal end portion (121) of the guiding cannula (103) may be configured to couple to the guiding plate (107; FIG. 1) of the lead insertion system (100; FIG. 1) described above. The proximal end portion (121) may also include, for example, a permanently fixed flange (124).

The guiding cannula (103) may also include a bent distal end portion (120) with a known radius (r). The bent distal end portion (120) includes a distal tip (123), as shown in FIG. 2. When the distal tip (123) of the guiding cannula (103) exits from the main cannula (102; FIG. 1), the distal tip (123) of the guiding cannula (103) follows the circumferential predetermined tract of the guiding cannula's distal end bend portion (120), which has a predetermined radius (r). In some alternative embodiments, the distal end portion (120) is straight.

As shown in FIG. 2, a microelectrode (110) may be inserted within the guiding cannula (103) with a distal tip (122) of the microelectrode (110) extending from the bent distal end portion (120) of the guiding cannula (103). The microelectrode (110) has an uninsulated tip (122) with a relatively small surface area configured to probe different areas of the brain and record or probe single cell activity. The remaining portions of the microelectrode (110) may be protected with an insulative material such as, but not limited to, a Teflon® coat and/or housed within a carrier protective tube made out of an insulative material such as, but not limited to, stainless steel.

As will be described in more detail below, the insertion depth within the brain of the distal tip (123) of the guiding cannula (103) may be adjusted with the depth adjustment mechanism (104; FIG. 1) mentioned above. The guiding cannula (103) may also be rotated about a vertical axis of the main cannula (102; FIG. 1) using the longitude adjustment plate (105; FIG. 1) such that 3-dimensional probing of the brain with the microelectrode (110) may be accomplished. Hence, an optimal site within the brain for deep brain stimulation may be precisely established by probing multiple points within the 3-dimensional range of the microelectrode (110).

Figure 3A:
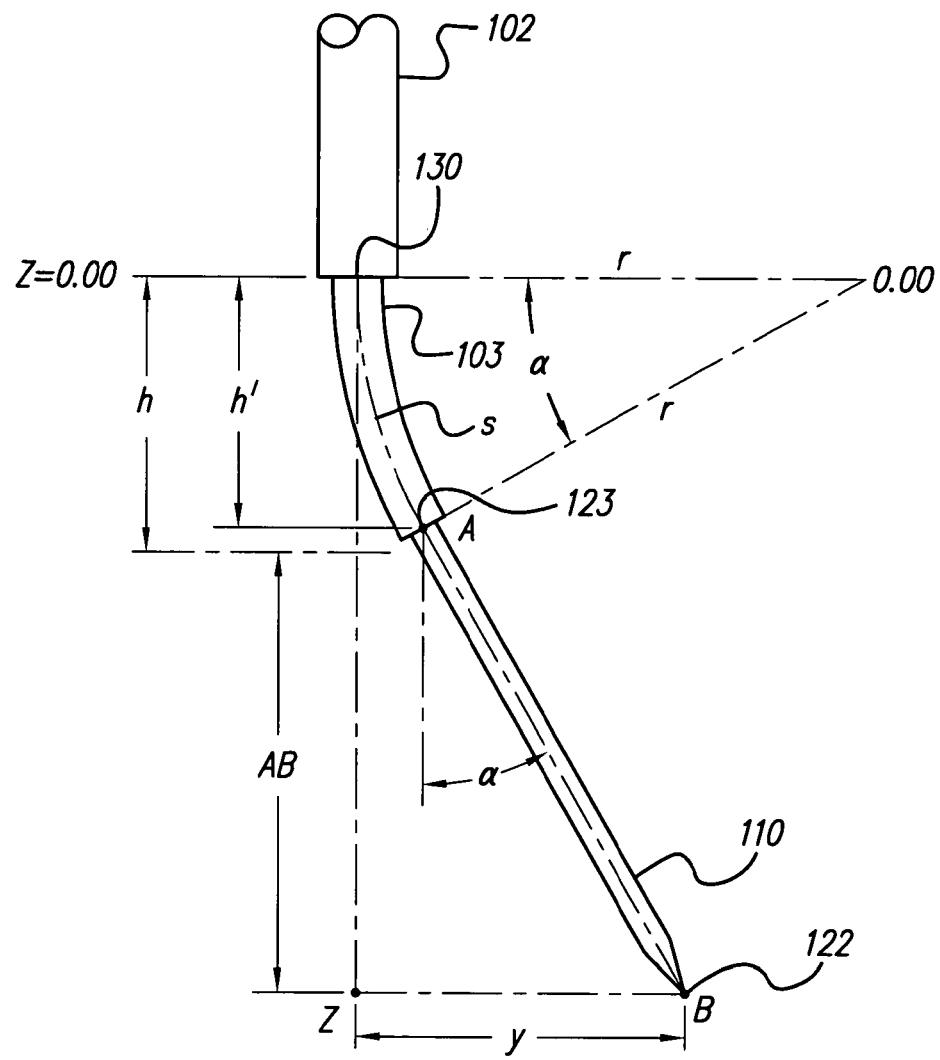
FIGS. 3A-3B show that the precise location of the microelectrode tip may be calculated using a number of mathematical formulas according to principles described herein.
Figure 3B:
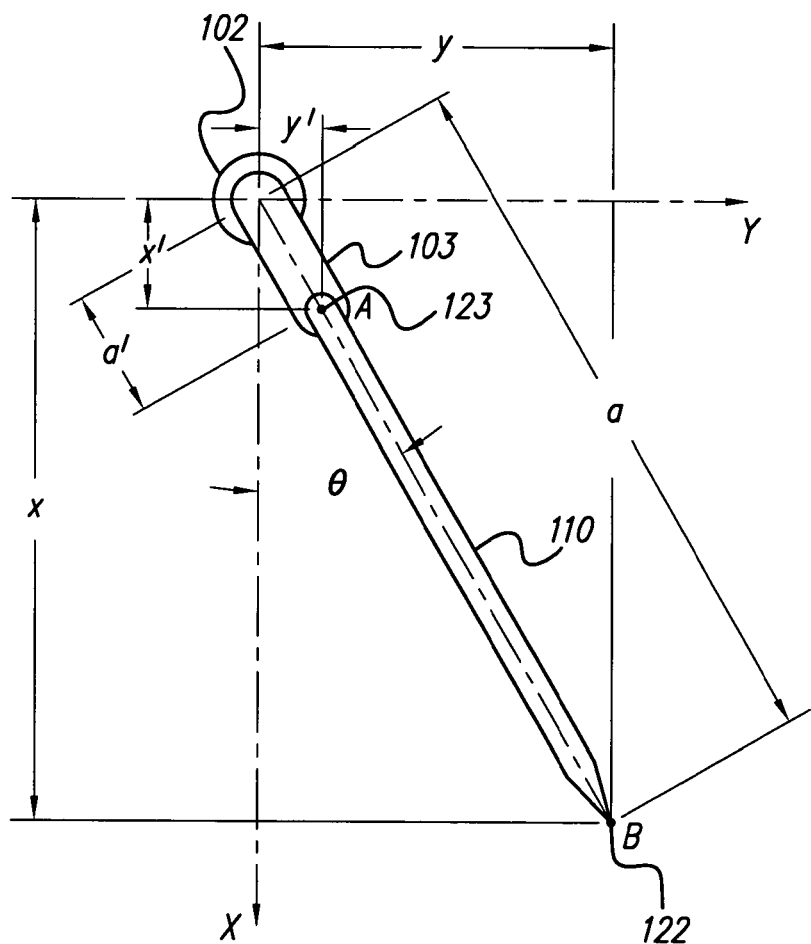

FIGS. 3A-3B show that the precise location of the microelectrode tip may be calculated using a number of mathematical formulas. FIG. 3A is a side view of the main cannula (102), the guiding cannula (103), and the microelectrode (110) and shows the depth, or vertical position, of the distal tip (123) of the guiding cannula (103) and the microelectrode tip (122). FIG. 3B is a top view of the main cannula (102), the guiding cannula (103), and the microelectrode (110) and shows the longitudinal position of the distal tip (123) of the guiding cannula (103) and the microelectrode tip (122).

In the following formulas, it is assumed that the coordinate of the distal end (130) of the main cannula (102) is 0,0,0. Table 1, shown below, defines a number of variables that will be used in the following formulas.

TABLE 1

Variable Definitions

| Variable | Definition |
|---|---|
| h | A maximum possible insertion depth of the distal tip (123) of the guiding cannula (103). The length of h is equivalent to the arc length s (the dashed center line of the guiding cannula (103)). |
| h + AB | A maximum possible insertion depth of the tip (122) of the microelectrode (110). |
| h' | The actual insertion depth of the distal tip (123) of the guiding cannula (103). |
| h' + AB · cosα | The actual insertion distance of the tip (122) of the microelectrode (110). |
| θ | The longitudinal angle, defined as an angle from an established direction at 0 degrees. |
| α | The exit angle for the microelectrode (110). |
| $A_{(x',y',z')}$ | The actual location of the distal tip (123) of the guiding cannula (103). The location has three dimensional components equal to x', y', and z'. |
| $B_{(x,y,z)}$ | The actual location of the distal tip (122) of the microelectrode (110). The location has three dimensional components equal to x, y, and z. |

The point labeled "A" in FIGS. 3A and 3B represents the location of the center of the distal tip (123) of the guiding cannula (103) and the point labeled "B" represents the location of the microelectrode tip (122). Point B may alternatively represent the location of the distal tip of a macroelectrode and/or a DBS lead that is inserted into the main cannula (102). Calculation of the coordinates for point A may include the following sequence of equations:

$$\alpha = 360\, h/\pi r^2;  \quad\text{Equation 1}$$

$$h' = r \cdot \sin\alpha = r \cdot \sin(360\, h/\pi r^2) \quad\text{Equation 2}$$

$$a' = r \cdot (1-\cos\alpha) = r \cdot (1-\cos(360\, h/\pi r^2)); \quad\text{Equation 3}$$

$$x' = a' \cdot \cos\theta; \quad\text{Equation 4}$$

$$y' = a' \cdot \sin\theta;\text{ and} \quad\text{Equation 5}$$

$$z' = h' = r \cdot \sin(360\, h/\pi r^2). \quad\text{Equation 6}$$

Therefore, the coordinates of A may be defined as $$A_{(x',y',z')} = A_{(a'\cdot\cos\theta,\, a'\cdot\sin\theta,\, r\cdot\sin(360\, h/\pi r^2))}.$$

Likewise, calculation of the coordinates for point B may include the following sequence of equations:

$$a = a' + AB\cdot\sin\alpha = r\cdot(1-\cos(360\, h/\pi r^2)) + AB\cdot\sin(360\, h/\pi r^2); \quad\text{Equation 1}$$

$$x = a\cdot\cos\theta; \quad\text{Equation 2}$$

$$y = a\cdot\sin\theta;\text{ and} \quad\text{Equation 3}$$

$$z = h' + AB\cdot\cos(360\, h/\pi r^2) = r\cdot\sin(360\, h/\pi r^2) + AB\cdot\cos(360\, h/\pi r^2) \quad\text{Equation 4}$$

Therefore, the coordinates of B may be defined as $$B_{(x,y,z)} = B_{(a\cdot\cos\theta,\, a\cdot\sin\theta,\, r\cdot\sin(360\, h/\pi r^2) + AB\cdot\cos(360\, h/\pi r^2))}.$$

The equations listed above may be modified to suit a particular coordinate system. Moreover, the equations listed above are merely exemplary of a set of equations that may be used to calculate the coordinates of the locations of the distal tip (123) of the guiding cannula (103) and the microelectrode tip (122). In some embodiments, the equations listed above, or an alternative set of equations, may be implemented and/or calculated using a computing device or computer program to acquire the precise coordinates of points A and B. The computing device and/or computer program may be used in conjunction with the depth adjustment mechanism (104; FIG. 1) and/or the longitude adjustment plate (105; FIG. 1) to automatically calculate the precise coordinates of the distal tip (123) of the guiding cannula (103) and the microelectrode tip (122). The calculated coordinates may then be used to position a macroelectrode and/or DBS lead in the brain at the optimal site within the brain for deep brain stimulation as determined by the probing performed by the microelectrode (110).

Figure 4C:
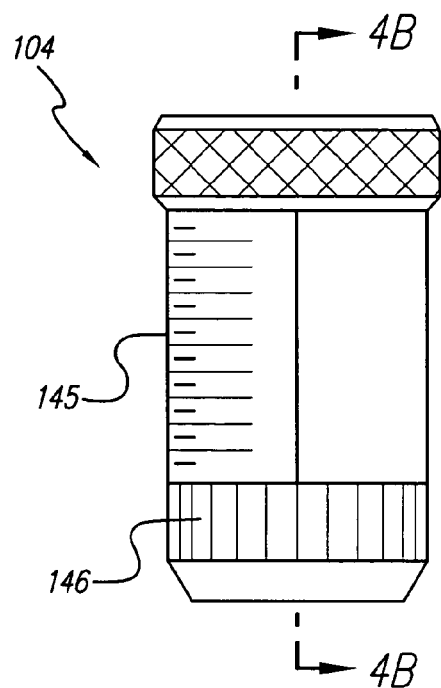
FIG. 4C is a top view of the depth adjustment mechanism of FIG. 4A according to principles described herein.
Figure 4C:
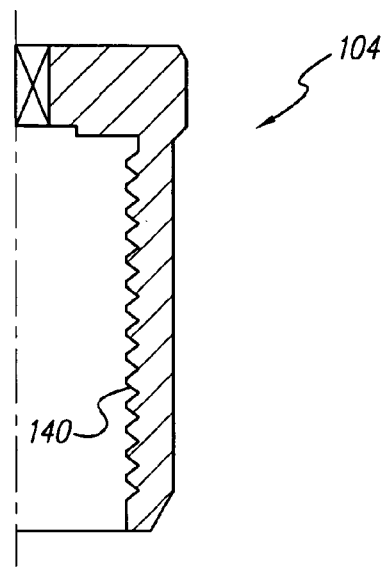
Figure 4C:
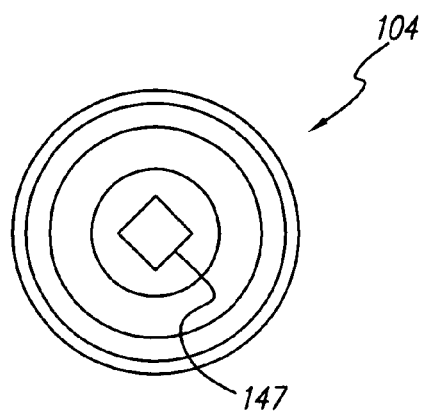

As mentioned, the insertion depth of the guiding cannula (103) within the brain may be adjusted with the depth adjustment mechanism (104; FIG. 1). FIG. 4A is a side view of an exemplary depth adjustment mechanism (104) that may be used to make precision adjustments to the depth of the guiding cannula (103). FIG. 4B is a half cross-sectional view of the depth adjustment mechanism (104) taken along the perspective line indicated in FIG. 4A. FIG. 4C is a top view of the depth adjustment mechanism (104) of FIG. 4A. As shown in FIGS. 4A and 4C, the depth adjustment mechanism (104) has a cylindrical form. FIG. 4B shows that the depth adjustment mechanism (104) has an internal thread (140). The internal thread (140) matches an external thread of the main base (101; FIG. 1), as described below in connection with FIGS. 5A and 5B. In some embodiments, the internal thread (140) is configured such that one complete revolution of the depth adjustment mechanism (104) equals a change in depth equal to one millimeter (mm). The change in depth per revolution of the depth adjustment mechanism (104) may vary as best serves a particular application.

As shown in FIG. 4A, the outer surface of the depth adjustment mechanism (104) may include a number of horizontal marks (145) for measuring an insertion depth of the guiding cannula (103; FIG. 1). A number of lateral marks (146) may also be included on the outer surface of the depth adjustment mechanism (104) for making very fine insertion depth adjustments and measurements. For example, ten evenly circumferentially distributed lateral marks (146) may be included on the outer surface of the depth adjustment mechanism (104). If one revolution of the depth adjustment mechanism (104) equals a change in depth equal to one millimeter, the radial distance between two adjacent lateral marks (146) is equal to one tenth of one revolution. Hence, the insertion depth of the guiding cannula (103; FIG. 1) may be adjusted with a resolution of 0.1 millimeters. It will be recognized that there may be any number of evenly distributed lateral marks (146) on the outer surface of the depth adjustment mechanism (104) as best serves a particular application.

An opening (147) in the top of the depth adjustment mechanism (104), as shown FIG. 4C, allows for the guiding cannula (103; FIG. 1), microelectrode (110; FIG. 1), macroelectrode, and/or DBS lead to pass through the lumen of the depth adjustment mechanism (104). The opening (147) may be rectangular in shape, as shown in FIG. 4C. However, it will be recognized that the opening (147) may have any shape as best serves a particular DBS lead insertion system (100; FIG. 1).

The depth adjustment mechanism (104) illustrated in connection with FIGS. 4A-4C is merely exemplary of any depth adjustment mechanism (104) that may be used to adjust and measure the depth of the guide cannula (103; FIG. 1) with a high degree of precision. Other configurations of the depth adjustment mechanism (104) may be used as best serves a particular DBS application. For example, the depth adjustment mechanism (104) may additionally or alternatively include a computerized motor or the like configured to adjust the insertion depth of the guiding cannula (103; FIG. 1).

Figure 5A:
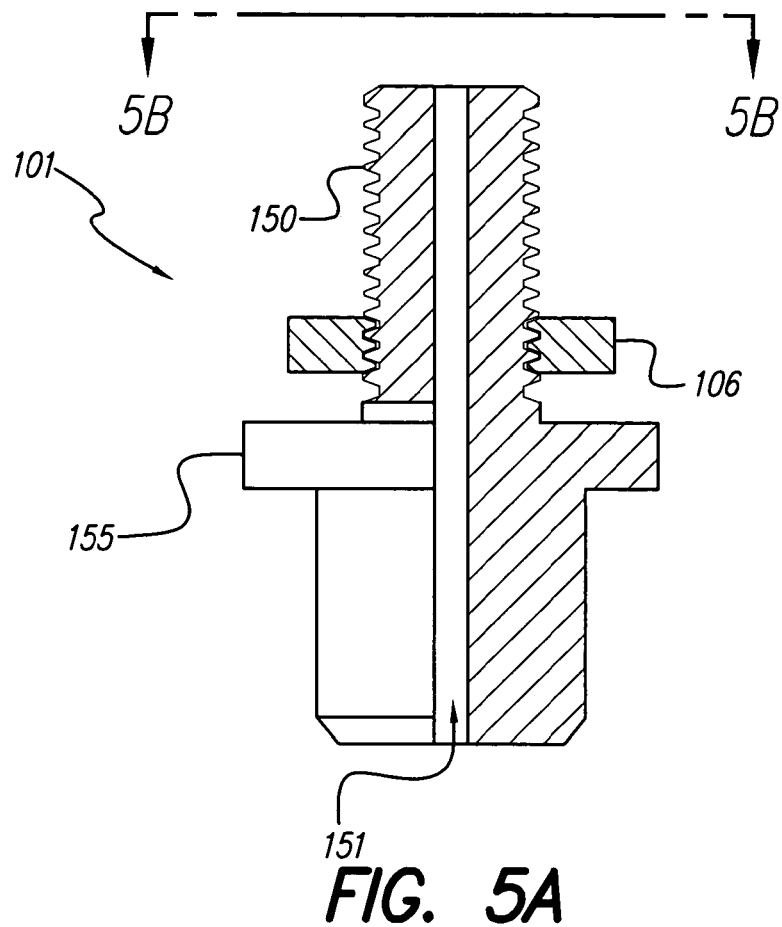
FIG. 5A is a cross sectional side view of the main base according to principles described herein.
Figure 5B:
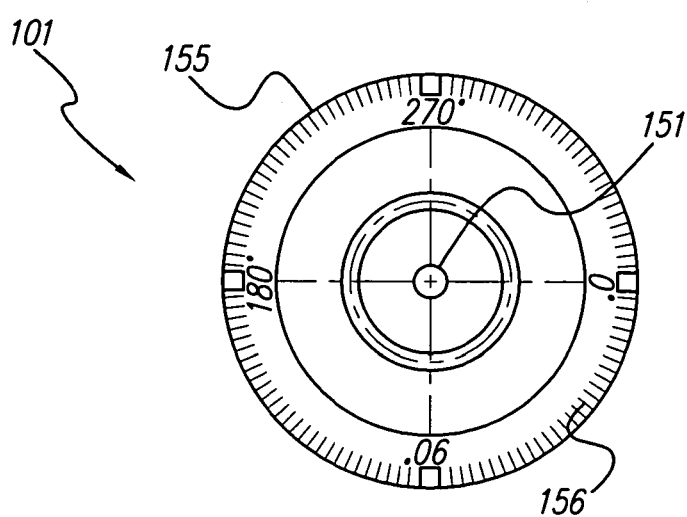
FIG. 5B is a top view of the main base taken along the perspective line indicated in FIG. 5A according to principles described herein.

FIGS. 5A and 5B illustrate an exemplary main base (101). FIG. 5A is a cross sectional side view of the main base (101) and FIG. 5B is a top view of the main base (101) taken along the perspective line indicated in FIG. 5A. As shown in FIG. 5A, the main base (101) includes an external thread (150) which matches and couples to the internal thread (140; FIG. 4B) of the depth adjustment mechanism (104; FIG. 4A). An opening (151) in the main base (101) allows the main cannula (102; FIG. 1) to pass through lumen of the main base (101) and extend into the brain.

As shown in FIG. 5B, the main base (101) may include a cylindrical ring (155) with a number of marks (156) located on a top surface of the ring (155) indicating a range of possible longitudinal angles of the distal tip (123; FIG. 2) of the guiding cannula (103; FIG. 2). For example, as shown in FIG. 5B, the cylindrical ring (155) includes a number of marks (156) indicating a range of longitudinal angles between zero and 360 degrees. The number of marks (156) indicating longitudinal angles may vary as best serves a particular DBS lead insertion system (100; FIG. 1). As will be described below, a notch on the longitude adjustment plate (105; FIG. 1) may be aligned to match a desired longitudinal angle as indicated by the marks (156) on the top surface of the cylindrical ring portion (155) of the main base (101).

Figure 6A:
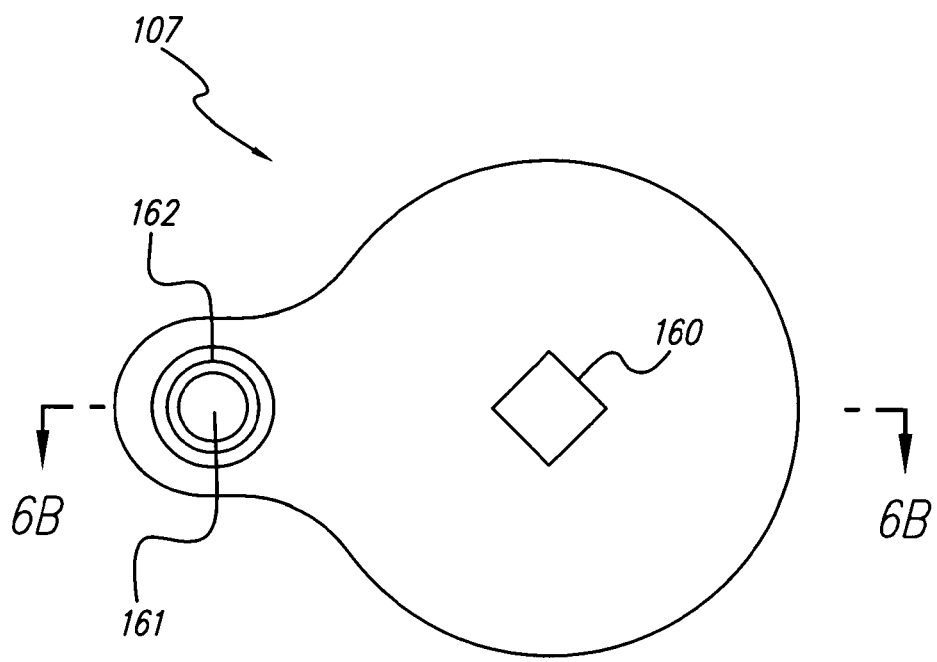
FIG. 6A is a top view of an exemplary guiding plate according to principles described herein.

FIG. 6A is a top view of an exemplary guiding plate (107). The guiding plate (107) includes an opening (160) which is used to couple the guiding plate (107) to the proximal end (121; FIG. 2) of the guiding cannula (103; FIG. 2). The opening (160) may have a rectangular shape, as shown in FIG. 6A, or any other shape as best serves a particular DBS lead insertion system (100; FIG. 1). The guiding plate (107) may be coupled to the retaining rail (108; FIG. 1) via a retaining lumen (161). As will be illustrated in more detail below, coupling the guiding plate (107) to the retaining rail (108; FIG. 1) ensures that the guiding cannula (103; FIG. 1) will be inserted into the brain at a desired longitudinal angle.

Figure 6B:
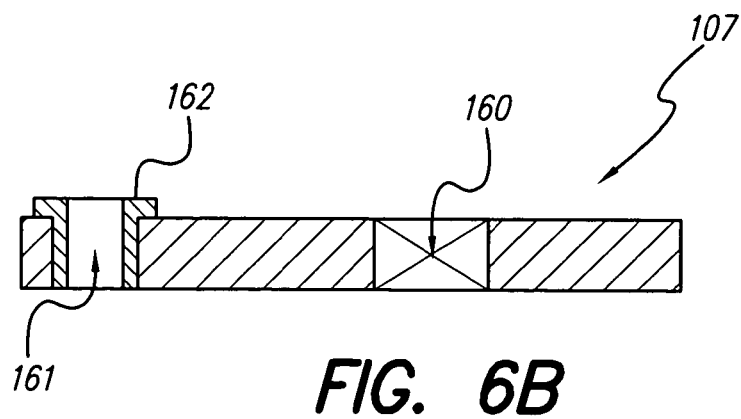
FIG. 6B is a cross-sectional side view of the guiding plate taken along the perspective line of FIG. 6A according to principles described herein.

FIG. 6B is a cross-sectional side view of the guiding plate (107). FIG. 6B shows that a guiding tube (162) or a sleeve may be inserted into the retaining lumen (161). The guiding tube (162) may be used to compensate for differences in the dimensions of the retaining lumen (161) and the retaining rail (108; FIG. 1). The guiding tube (162) may be made out of any suitable material. In some embodiments, the guiding tube (162) may be made out of a plastic or material configured to conform to the dimensions of the retaining rail (108; FIG. 1). In some alternative embodiments, the guiding plate (107) is coupled to the retaining rail (108; FIG. 1) without the use of the guiding tube (162).

Figure 7:
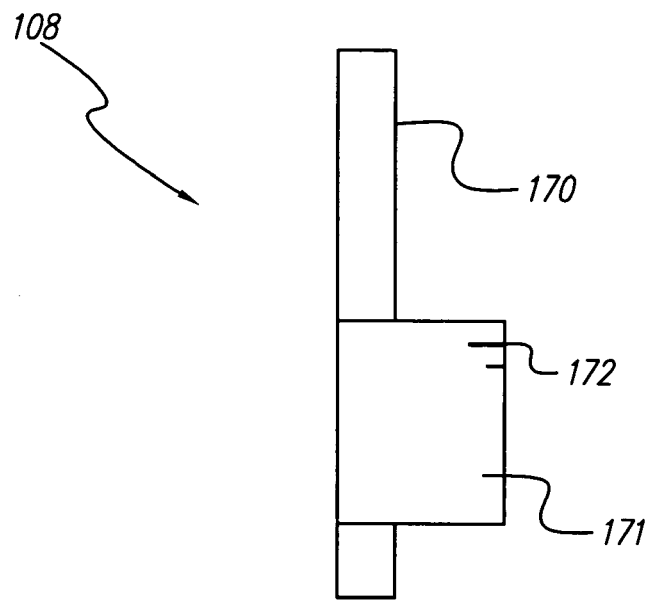
FIG. 7 illustrates an exemplary retaining rail according to principles described herein.

FIG. 7 illustrates an exemplary retaining rail (108). The retaining rail (108) includes a straight pin (170) and a wing member (171). The straight pin (170) may be made out of any material having high dimensional and geometrical tolerances in order to maintain a precise longitudinal angle for the guiding cannula (103; FIG. 1). For example, the straight pin (170) may be made out of stainless steel. The straight pin (170) has a circumference small enough such that straight pin (170) fits into the guiding tube (162; FIG. 6B) and/or the retaining lumen (161; FIG. 6B). In this manner, the straight pin (170) is used to couple the retaining rail (108) to the guiding plate (107; FIG. 6A).

The wing member (171) of the retaining rail (108) may extend in a direction perpendicular to the axis of the straight pin (170), as shown in FIG. 7. The wing member (171) may include a horizontal reference mark (172) that may be used to initially position the depth adjustment mechanism (104; FIG. 4A). The horizontal reference mark (172) is also used in connection with the horizontal marks (145; FIG. 4A) to measure the insertion depth of the guiding cannula (103; FIG. 1).

For example, the depth adjustment mechanism (104; FIG. 4A) may be adjusted such that a particular horizontal mark (145; FIG. 4A) lines up with the horizontal reference mark (172) such that a surgeon knows the exact insertion depth of the guiding cannula (103; FIG. 1). In some alternative embodiments, the retaining rail (108) only includes the straight pin (170). In these embodiments, the straight pin (170) may include the horizontal reference mark (172).

Figure 8:
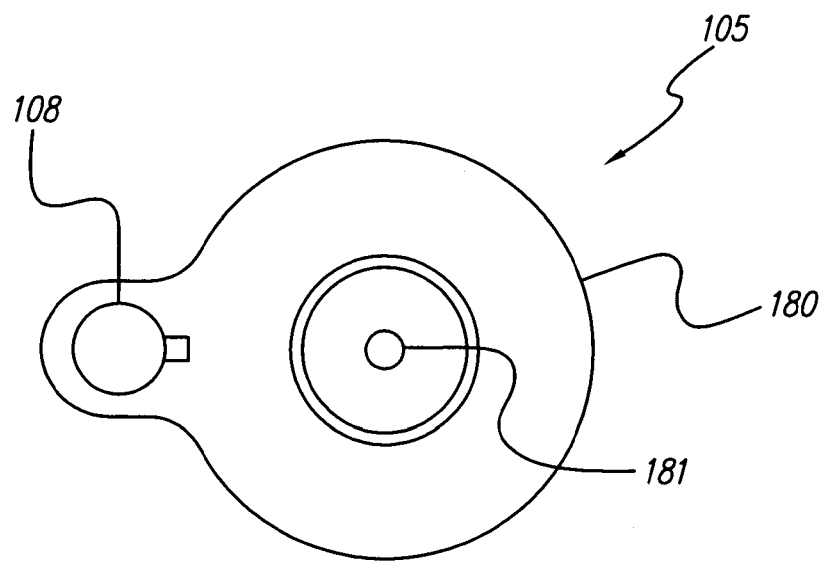
FIG. 8 is a top view of an exemplary longitude adjustment plate according to principles described herein.

FIG. 8 is a top view of an exemplary longitude adjustment plate (105). As shown in FIG. 8, the longitude adjustment plate (105) is in the shape of a cylindrical ring and is configured to rotate about a central vertical axis (181). As will be described in more detail below, the longitude adjustment plate (105) includes a notch (180) that may be aligned with one of the marks (156; FIG. 5B) on the top surface of the cylindrical ring portion (155; FIG. 5B) of the main base (101; FIG. 5B) to adjust the longitudinal angle of the guiding cannula (103; FIG. 1).

Returning to FIG. 1, it can be seen that the longitude adjustment plate (105) is coupled to the retaining rail (108). The retaining rail (108), in turn, is coupled to the guiding plate (107). The guiding plate (107), in turn, is coupled to the proximal end portion (121; FIG. 2) of the guiding cannula (103). Hence, a rotation of the longitude adjustment plate (105) shown in FIG. 8 about the central vertical axis (181) rotates the guiding cannula (103; FIG. 1) about the same central vertical axis (181). In this manner, the longitudinal angle, θ, of the distal tip (123; FIG. 1) of the guiding cannula (103; FIG. 1), as described above in connection with FIGS. 3A-3B, may be adjusted to be equal to any angle between zero and 360 degrees. The longitudinal locking mechanism (106; FIG. 1) may be tightened to prevent the longitude adjustment plate (105) from rotating about its central vertical axis (181), thus locking the longitudinal angle of the distal tip (123; FIG. 1) of the guiding cannula (103; FIG. 1) in place. When it is desired to adjust the longitudinal angle, the longitudinal locking mechanism (106; FIG. 1) is loosened and the longitude adjustment plate (105) is rotated until the notch (180) is aligned with the desired longitudinal angle as indicated by the marks (156; FIG. 5B) on the top surface of the cylindrical ring portion (155; FIG. 5B) of the main base (101; FIG. 5B).

The longitude adjustment plate (105) of FIG. 8 is merely illustrative of the many devices that may be used to adjust the longitudinal angle of the guiding cannula (103; FIG. 1). Alternative longitudinal angle adjustment devices that may be used to adjust the longitudinal angle of the guiding cannula (103; FIG. 1) include, for example, a computerized motor or the like configured to adjust the longitudinal angle of the guiding cannula (103; FIG. 1).

Figure 9:
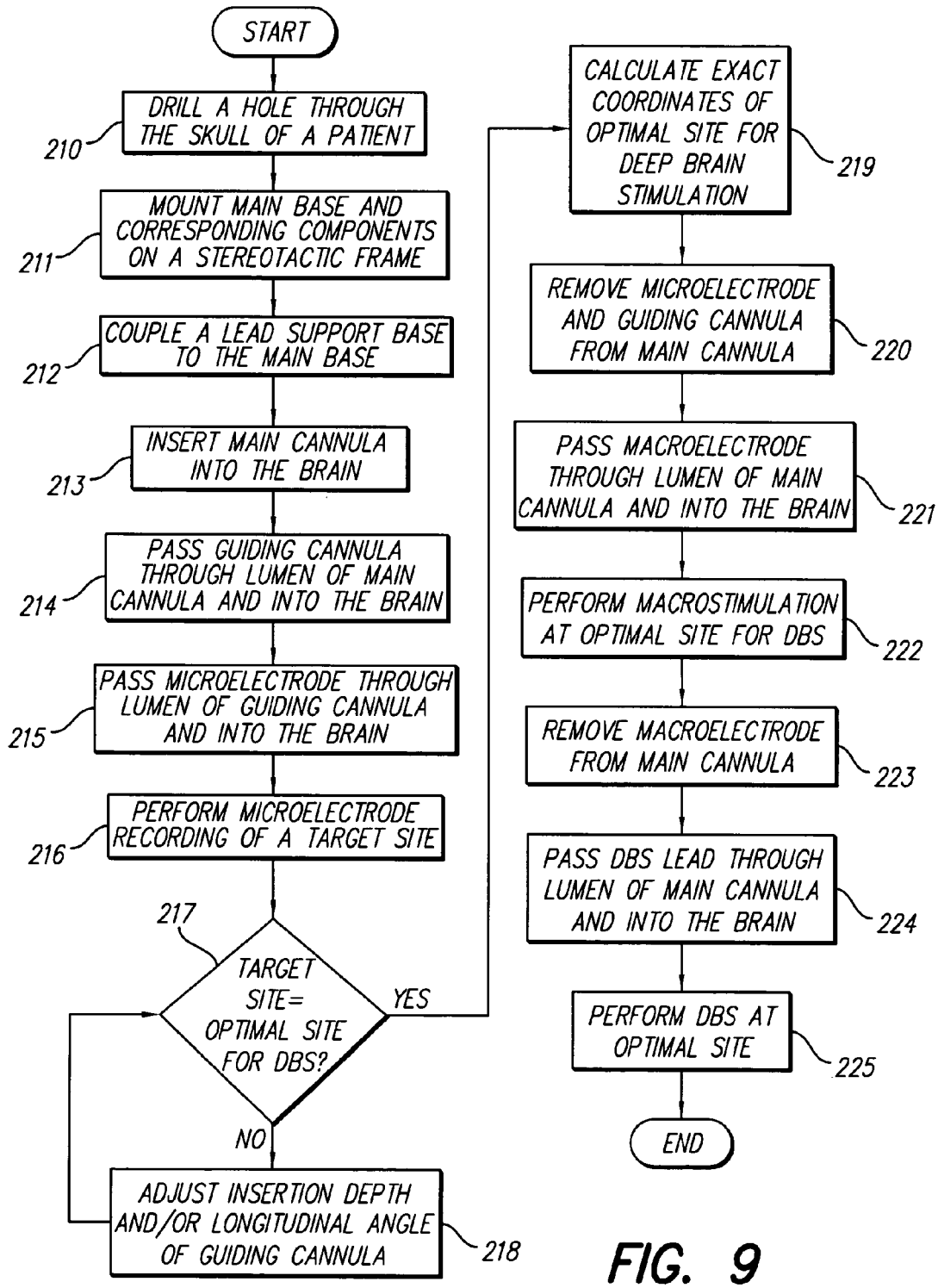
FIG. 9 is a flow chart illustration an exemplary method of locating an optimal site within the brain of a patient for deep brain stimulation according to principles described herein.

By way of example, a method of locating an optimal site within the brain of a patient for deep brain stimulation will be described in connection with the flow chart of FIG. 9 and the illustrations FIGS. 10A-10G and may be carried out according to the following sequence of procedures. The steps listed below may be modified, removed, reordered, and/or added to as best serves a particular application.

Figure 10A:
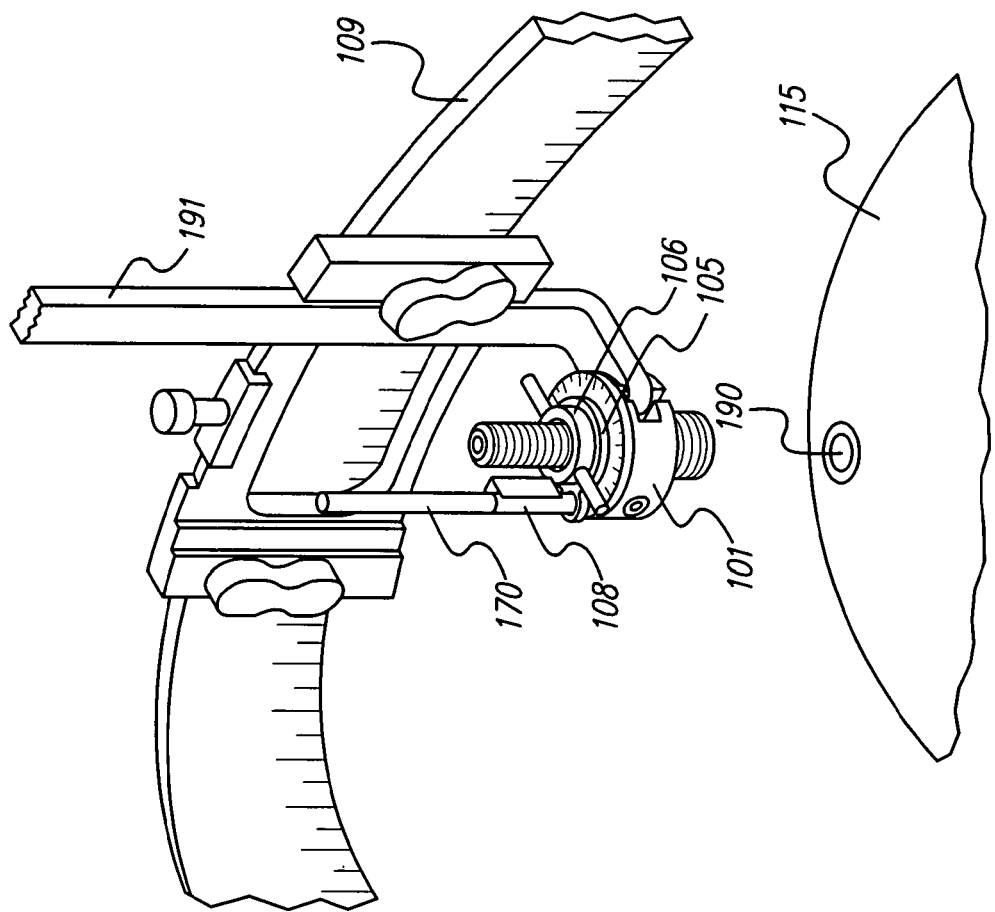
FIGS. 10A-10G illustrate various steps in an exemplary method of locating an optimal site within the brain of a patient for deep brain stimulation according to principles described herein.

1. A hole is drilled through the skull of a patient (step 210; FIG. 9). FIG. 10A illustrates an exemplary hole (190) that may be drilled through the skull (115). The hole (190) may be of a suitable size such that the main cannula (102; FIG. 1) may be inserted through the hole (190) and into the brain of the patient. For example, the hole (190) may be substantially equal to or less than eight millimeters in diameter. The hole (190) may be secured by a burr hole plug shell, as shown.

2. The main base (101; FIG. 10A) and corresponding components are mounted on a stereotactic frame (109) (step 211; FIG. 9). As shown in FIG. 10A, the main base (101), longitude adjustment plate (105), longitudinal locking mechanism (106), and retaining rail (108) are mounted on the stereotactic frame (109) using any suitable mounting device (191). FIG. 10A shows that main base (101) and related components are positioned directly above the hole (190) such that the main cannula (102; FIG. 1) may be inserted into the hole (190).

Figure 10B:
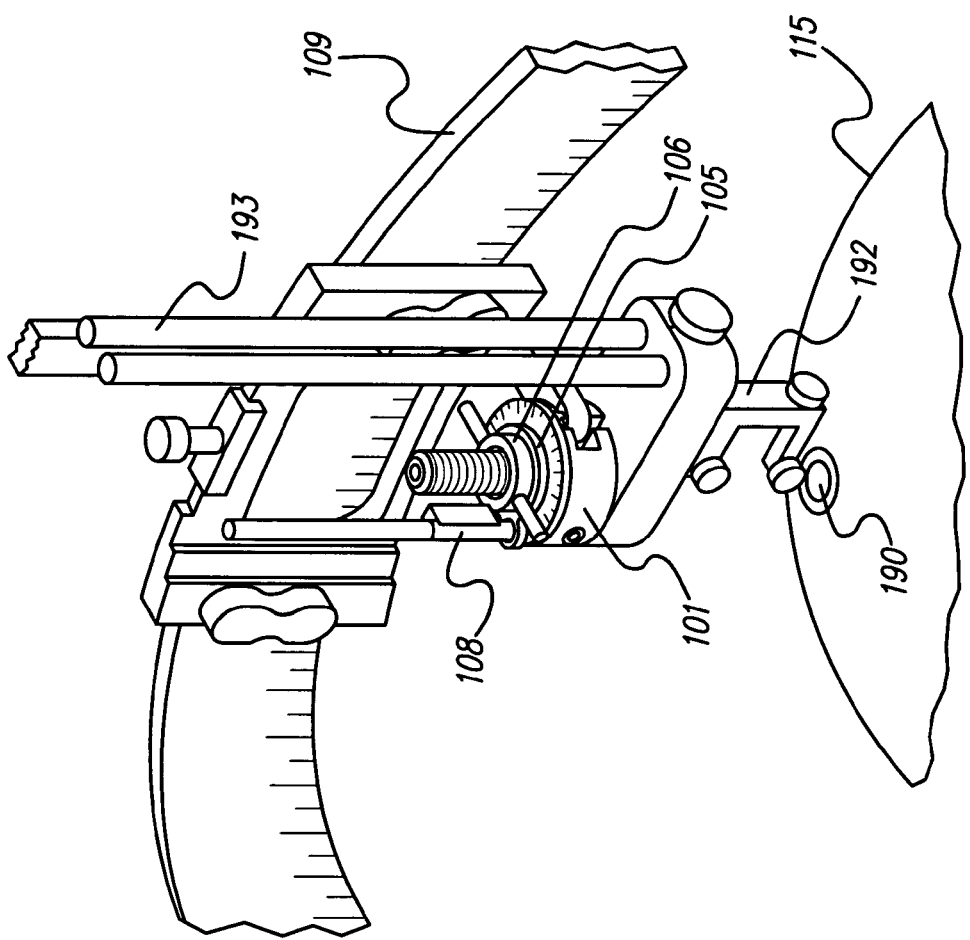

3. A lead support base (193; FIG. 10B) is coupled to the main base (101) (step 212; FIG. 9). The lead support base (193) may be any structure configured to support a DBS lead as it is being inserted into the brain. A main cannula anchor device (192) may also be coupled to the main base (101). The main cannula anchor device (192) is configured to lock the main cannula (102; FIG. 1) into place once the main cannula (102; FIG. 1) has been inserted into the brain.

Figure 10C:
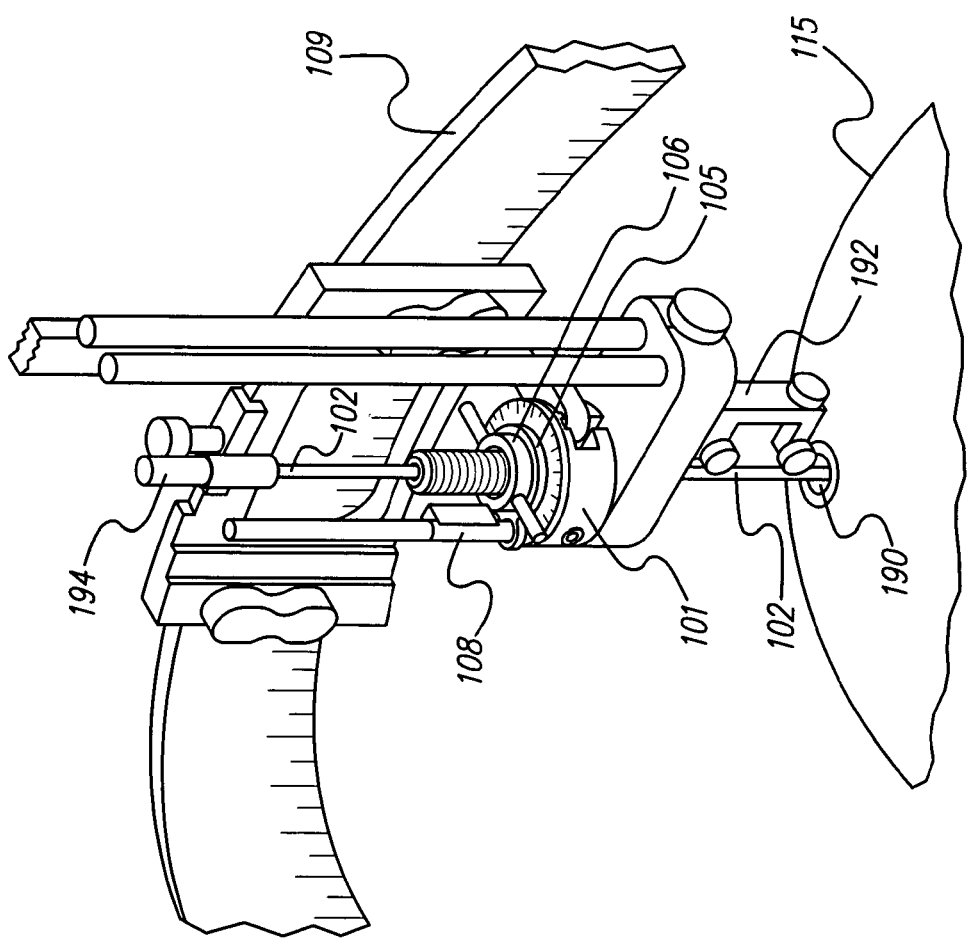

4. The main cannula (102; FIG. 10C) is inserted into the brain (step 213; FIG. 9). As shown in FIG. 10C, the main cannula (102) and a stylet (194) are passed through the lumen of the main base (101) and inserted into the brain. The stylet (194) is configured to precisely fill the lumen of the main cannula (102) to prevent coring of tissue while creating an entry path into the brain. The main cannula (102), with stylet (104) inserted, is advanced into the brain to a desired distance above a target site for microelectrode recording. For example, the main cannula (102) may be advanced into the brain to a distance substantially equal to 20 mm above the target site for microelectrode recording. Once the main cannula (102) is appropriately positioned, the main cannula (102) is clamped into place with the main cannula anchor device (192) and the stylet (194) is removed. If needed, a spacer cannula may first be inserted into the lumen of the main cannula (102).

Figure 10D:
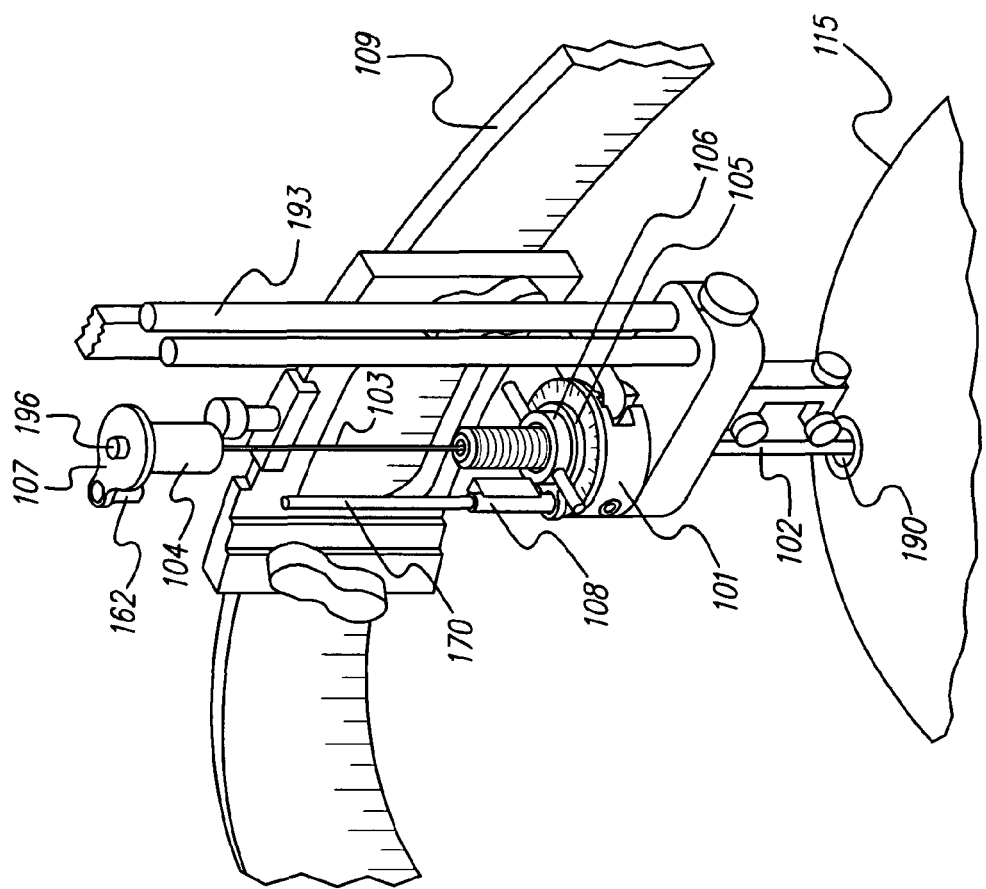
Figure 10E:
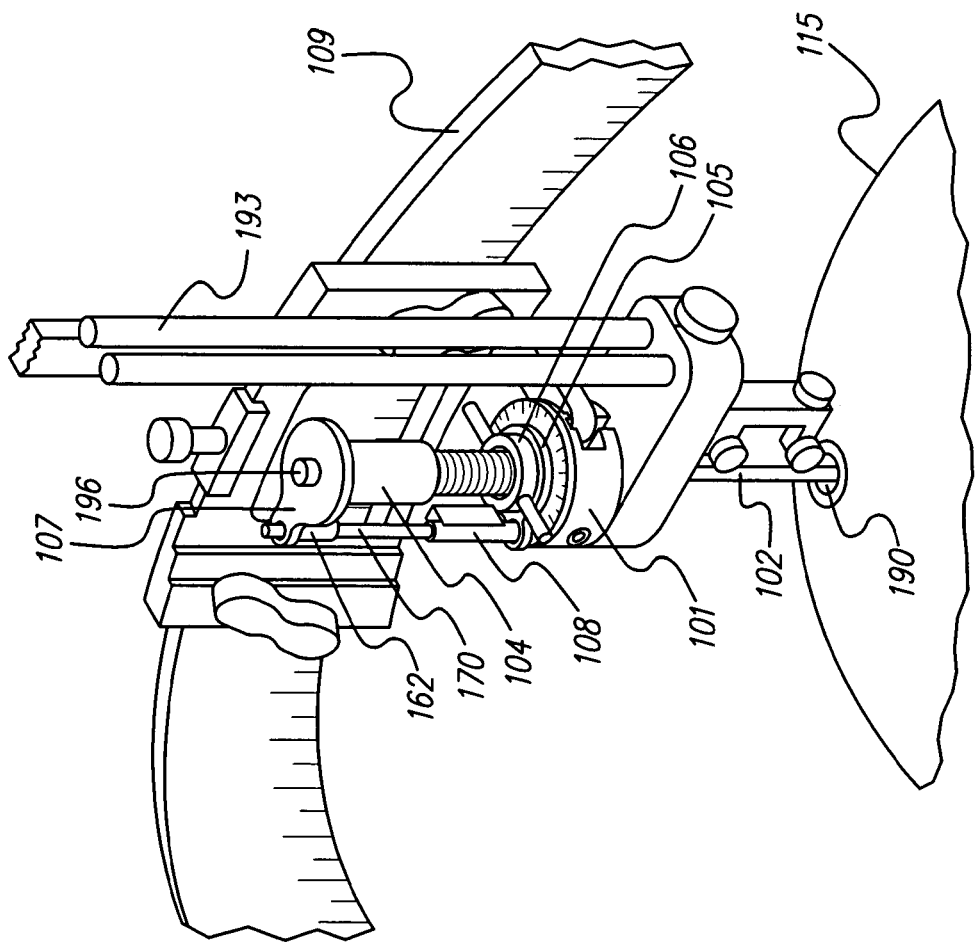

5. As shown in FIGS. 10D and 10E, the guiding cannula (103), also known as the microstimulator-guiding cannula, is then passed through the lumen of the depth adjustment mechanism (104), through the lumen of the main cannula (102), and into the brain (step 214; FIG. 9). A stylet may alternatively be used to assist in the placement of the guiding cannula (103) into the brain. The guiding cannula (103) may be coupled to the guiding plate (107) using a securing nut (196). FIG. 10E shows that the guiding plate (107) includes a guiding tube (162) that slides onto the straight pin (170) of the retaining rail (108).

The depth of the distal tip (123; FIG. 1) of the guiding cannula (103) may initially be set to be equal to the depth of the distal end of the main cannula (102). In some embodiments, the depth of the distal tip (123; FIG. 1) of the guiding cannula (103) is set to be equal to the depth of the distal end of the main cannula (102) by rotating the depth adjustment mechanism (104) in a clockwise direction until a specified circumferentially engraved marking on the depth adjustment mechanism (104) becomes aligned with a horizontal reference mark (172; FIG. 7) located on the wing member (171) of the retaining rail (108). The depth of the guiding cannula (103) may then be adjusted to any desired depth by further rotating the depth adjustment mechanism (104).

Figure 10F:
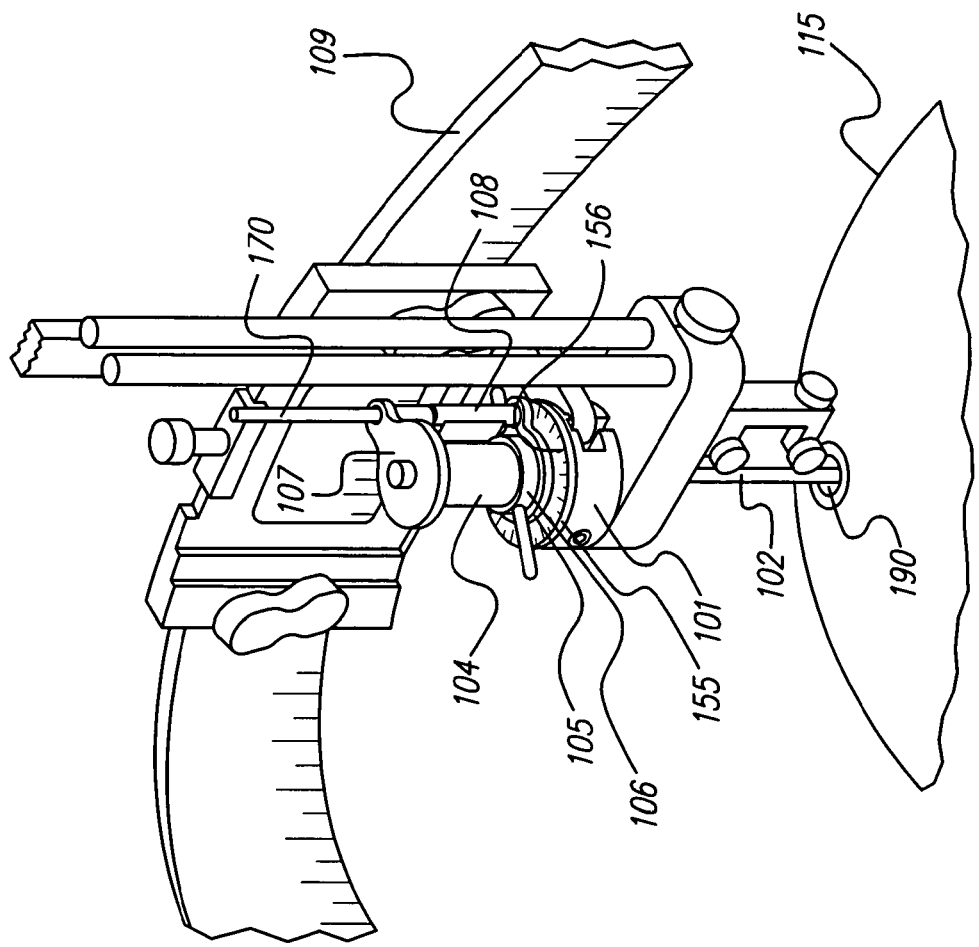
Figure 10G:
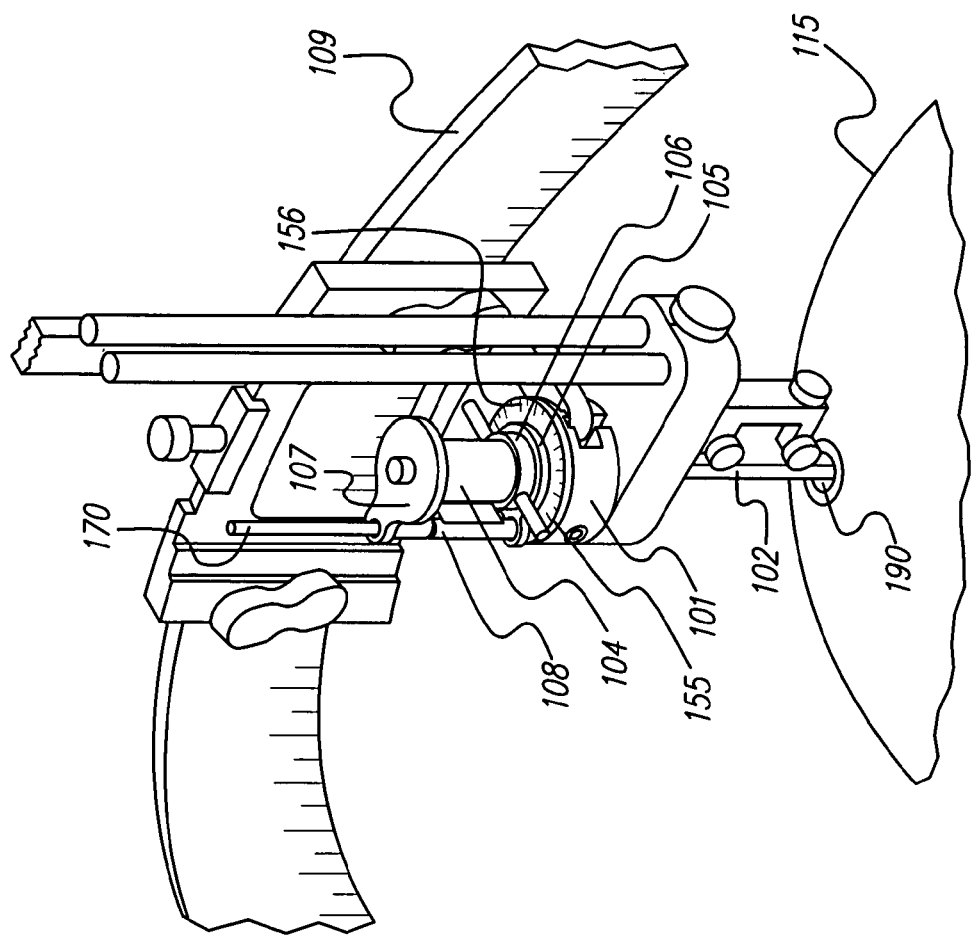

A desired longitudinal angle of the guiding cannula (103) may then be set, as illustrated in FIGS. 10F and 10G. The longitudinal locking mechanism (106) is first loosened. The longitude adjustment plate (105) is then rotated to a desired longitudinal angle as indicated by the marks (156) on the cylindrical ring portion (155) of the main base (101), thereby rotating the distal tip (123) of the guiding cannula (103) within and within and relative to the main cannula (102) to set the longitudinal angle. The longitudinal locking mechanism (106) is then tightened. FIG. 10F shows the longitude adjustment plate (105) in a first position and FIG. 10G shows that the longitude adjustment plate (105) has been rotated to a second position.

6. When the initially desired depth and longitudinal angle of the guiding cannula (103) have been set, the microelectrode (110) is passed through the lumen of the guiding cannula (103) and into the brain (step 215; FIG. 9). The microelectrode (110) may be passed through the lumen of the guiding cannula (103) such that the distal tip (122; FIG. 1) of the microelectrode (110) protrudes a predetermined distance from the distal tip (123; FIG. 1) of the guiding cannula (103) using any technique known in the art.

7. Microelectrode recording is then performed by the microelectrode (110) at a target site (step 216; FIG. 9).

8. The depth and longitudinal angle of the guiding cannula (103) may be further adjusted such that the microelectrode (110) records or probes a number of different target sites at varying depths and longitudinal angles until an optimal site within the brain for deep brain stimulation has been located (steps 217, 218; FIG. 9). In some embodiments, the step of adjusting the depth and longitudinal angle of the guiding cannula (103) may include one or more of the following sub-steps. First, the microelectrode (110) is removed from the guiding cannula (103). The guiding cannula (103) is adjusted such that the depth of the distal tip (123; FIG. 1) of the guiding cannula (103) is once again equal to or less than the depth of the distal end of the main cannula (102). The longitudinal angle is then adjusted to the new desired longitudinal angle. The depth of the guiding cannula (103) may then be adjusted to the new desired depth. The microelectrode (110) may then be reinserted into the guiding cannula (103) and record or probe the new target site.

9. When an optimal site within the brain for deep brain stimulation has been located by the microelectrode recording process (YES; step 217), the exact coordinates of the optimal site are calculated using the equations given above (step 219; FIG. 9). These exact coordinates may be subsequently used to insert a macroelectrode and/or DBS lead into the brain at the optimal site as determined by the microelectrode recording.

10. The microelectrode (110) and guiding cannula (103) are removed from the DBS lead insertion system (100; FIG. 1) (step 220; FIG. 9). The main cannula (102) remains inserted into the brain.

11. A macroelectrode or a second guiding cannula (also known as a macroelectrode-guiding cannula) containing the macroelectrode may then be passed through the lumen of the main cannula (102) and into the brain (step 221; FIG. 9) such that the macroelectrode performs macrostimulation at the optimal site for deep brain stimulation as determined previously by the microelectrode (110) probing (step 222; FIG. 9). The microstimulator-guiding cannula may have a bent distal end portion similar to the bent distal end portion (120; FIG. 2) of the microstimulator-guiding cannula (103).

12. The macroelectrode is removed from the lumen of the main cannula (102; FIG. 1) (step 223; FIG. 9).

13. A DBS lead and/or catheter may be inserted into the brain via the lumen of the main cannula (102) (step 224; FIG. 9). The second guiding cannula (also known as the macrostimulator-guiding cannula) described in connection with step 11 above or a third guiding cannula (also known as a lead-guiding cannula) may be used in some embodiments to facilitate the insertion of the DBS lead and/or catheter into the brain.

14. Deep brain stimulation is applied to the optimal site within the brain for deep brain stimulation via the DBS lead and/or catheter (step 225; FIG. 9).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of delivering a medical device within a brain of a patient, said method comprising:
   inserting a distal portion of a main cannula into said brain, said main cannula having a longitudinal axis and a lumen;
   positioning a guiding cannula in said lumen of said main cannula, said guiding cannula comprising a lumen and a distal end portion;
   adjusting an insertion depth of said guiding cannula, wherein said distal end portion of said guiding cannula is bent as it is advanced from said main cannula, such that a longitudinal angle is formed between a line perpendicular to, and extending through, said longitudinal axis, and said bent distal end portion of said guiding cannula when projected within a plane that includes said line;
   setting said longitudinal angle by rotating said distal end portion within and relative to said main cannula prior to advancing said distal end portion from said main cannula; and
   passing a medical device through said lumen of said guiding cannula into said brain.

2. The method of claim 1, wherein said medical device is at least one of a macroelectrode and a stimulation lead.

3. The method of claim 1, wherein said medical device is a microelectrode, the method further comprising locating a stimulation site within said brain using the microelectrode.

4. The method of claim 3, wherein said stimulation site is an optimum stimulation site.

5. The method of claim 3, further comprising calculating at least one coordinate corresponding to said stimulation site.

6. The method of claim 5, wherein said step of calculating said at least one coordinate further comprises calculating said at least one coordinate with reference to a location corresponding to a distal end of said main cannula.

7. The method of claim 5, wherein said step of calculating said location of said stimulation site comprises calculating coordinates of said stimulation site according to the following equation, said location represented by B(x,y,z):

$$B_{(x,y,z)} = B_{(a \cdot \cos \theta, a \cdot \sin \theta, r \cdot \sin(360\ h/\pi r^2) + AB \cdot \cos(360\ h/\pi r^2))};$$

wherein x is a first dimensional coordinate substantially equal to $a \cdot \cos \theta$, y is a second dimensional coordinate substantially equal to $a \cdot \sin \theta$, and z is a third dimensional coordinate substantially equal to $r \cdot \sin(360\ h/\pi r^2) + AB \cdot \cos(360\ h/\pi r^2)$;

wherein r represents a radius of said bent distal end portion of said guiding cannula, $\theta$ represents said longitudinal angle, h represents a maximum possible insertion depth of a distal tip of said guiding cannula, and AB represents a maximum possible insertion depth of a tip of said microelectrode minus h.

8. The method of claim 5, further comprising removing said microelectrode and inserting a macroelectrode or deep brain stimulation (DBS) lead such that a distal tip of said macroelectrode or DBS lead is positioned at said stimulation site.

9. The method of claim 8, further comprising positioning a distal end of said at least one of said macroelectrode and said DBS lead within said brain in accordance with said at least one coordinate.

10. The method of claim 1, wherein said distal portion is pre-shaped to bend.

11. The method of claim 1, further comprising mounting a stereotactic frame to said patient, wherein said distal portion of said main cannula is inserted into said brain relative to said stereotactic frame.

12. The method of claim 1, further comprising:
locating a stimulation site within said brain; and
conveying stimulation energy to said stimulation site.

13. The method of claim 1, further comprising:
withdrawing said distal end portion of said guiding cannula into said main cannula; and
setting said longitudinal angle again by rotating said distal end portion of said guiding cannula within and relative to said main cannula after said distal end portion of said guiding cannula is withdrawn into said main cannula; and
advancing said withdrawn distal end portion of said guiding cannula from said main cannula.

14. A method of locating an optimal stimulation site within a brain of a patient, said method comprising:
(a) inserting a portion of a main cannula into said brain, said main cannula having a longitudinal axis and a lumen;
(b) inserting a portion of a guiding cannula into said lumen of said main cannula, said guiding cannula having a lumen and a distal end portion configured to bend;
(c) adjusting an insertion depth of said guiding cannula, wherein said distal end portion of said guiding cannula is bent as it is advanced from said main cannula, such that a longitudinal angle is formed between a line perpendicular to, and extending through, said longitudinal axis, and said bent distal end portion of said guiding cannula when projected within a plane that includes said line;
(d) setting said longitudinal angle by rotating said distal end portion of said guiding cannula within and relative to said main cannula prior to advancing said distal end portion of said guiding cannula from said main cannula;
(e) passing a microelectrode through said lumen of said guiding cannula into said brain such that said microelectrode locates said optimal stimulation site; and
(f) wherein if an optimal stimulation site is not located by said microelectrode, said method comprises retracting said microelectrode and said guiding cannula out of said brain and repeating steps (c), (d), (e), and (f).

15. The method of claim 14, further comprising calculating a location of said optimal stimulation site.

16. The method of claim 15, wherein said step of calculating said location of said optimal stimulation site further comprises calculating said location with reference to a location corresponding to a distal end of said main cannula.

17. The method of claim 15, wherein said step of calculating said location of said optimal stimulation site comprises calculating coordinates of said optimal stimulation site according to the following equation, said location represented by B(x,y,z):

$$B_{(x,y,z)} = B_{(a \cdot \cos\theta, a \cdot \sin\theta, r \cdot \sin(360\, h/\pi r^2) + AB \cdot \cos(360\, h/\pi r^2))};$$

wherein x is a first dimensional coordinate substantially equal to $a \cdot \cos\theta$, y is a second dimensional coordinate substantially equal to $a \cdot \sin\theta$, and z is a third dimensional coordinate substantially equal to $r \cdot \sin(360\, h/\pi r^2) + AB \cdot \cos(360\, h/\pi r^2)$;
wherein r represents a radius of said bent distal end portion of said guiding cannula, $\theta$ represents said longitudinal angle, h represents a maximum possible insertion depth of a distal tip of said guiding cannula, and AB represents a maximum possible insertion depth of a tip of said microelectrode minus h.

18. The method of claim 15, further comprising removing said microelectrode and inserting a macroelectrode or DBS lead such that a distal tip of said macroelectrode or said DBS lead is positioned at said calculated optimal stimulation site.

19. The method of claim 18, further comprising passing a distal end of said macroelectrode or said DBS lead through said lumen of said main cannula and into said brain at said optimal stimulation site.

20. The method of claim 14, wherein said bent distal portion is pre-shaped.

21. The method of claim 14, further comprising mounting a stereotactic frame to said patient, wherein said distal portion of said main cannula is inserted into said brain relative to said stereotactic frame.

22. The method of claim 14, further comprising conveying stimulation energy to said optimal stimulation site.

23. The method of claim 14, further comprising:
withdrawing said distal end portion of said quidinq cannula into said main cannula; and
setting said longitudinal angle again by rotating said distal end portion of said guiding cannula within and relative to said main cannula after said distal end portion of said guiding cannula is withdrawn into said main cannula; and
advancing said withdrawn distal end portion of said guiding cannula from said main cannula.

* * * * *